United States Patent
Kostlan et al.

(10) Patent No.: US 7,615,230 B2
(45) Date of Patent: Nov. 10, 2009

(54) METHOD FOR DECREASING SEBUM PRODUCTION

(75) Inventors: Catherine R. Kostlan, Saline, MI (US); Raj Neil Raheja, Ann Arbor, MI (US); Meera Tugnait, Ann Arbor, MI (US); Kimberly Wade, Brighton, MI (US)

(73) Assignee: Graceway Pharmaceuticals, LLC, Bristol, TN (US)

( * ) Notice: Subject to any disclaimer, the term of this patent is extended or adjusted under 35 U.S.C. 154(b) by 912 days.

(21) Appl. No.: 10/958,306

(22) Filed: Oct. 5, 2004

(65) Prior Publication Data

US 2005/0079144 A1 Apr. 14, 2005

Related U.S. Application Data

(60) Provisional application No. 60/509,984, filed on Oct. 9, 2003.

(51) Int. Cl.
*A61K 8/02* (2006.01)
*A61K 8/00* (2006.01)
*A61K 31/44* (2006.01)

(52) U.S. Cl. .................. 424/401; 424/69; 424/70.1; 514/357; 514/442; 514/616

(58) Field of Classification Search .................. None
See application file for complete search history.

(56) References Cited

U.S. PATENT DOCUMENTS

| 4,299,845 | A | | 11/1981 | Loebenberg et al. |
| 5,656,634 | A | | 8/1997 | Chang et al. ............... 514/255 |
| 6,133,326 | A | * | 10/2000 | Mayne ....................... 514/346 |

FOREIGN PATENT DOCUMENTS

| EP | 0 433 622 A2 | | 6/1991 |
| EP | 433662 | * | 6/1991 |
| WO | WO 01/56556 A2 | | 8/2001 |

OTHER PUBLICATIONS

Yagyu et al., Absence of ACAT-1 Attenuates Atherosclerosis but Causes Dry Eye and Cutaneous Xanthomatosis in Mice with Congenital Hyperlipidemia, Journal of Biological Chemistry, pp. 21324-21330, vol. 275/28, Apr. 20, 2000.
Burkhardt, J., et al., "Effect of Topical Treatment with CP-118,313 in Dogs on the Morphology of Sebaceous Glands—Study of the Dose Response Relationship", Study #DI-99-109, 115, 123.

* cited by examiner

*Primary Examiner*—Lakshmi S Channavajjala
(74) *Attorney, Agent, or Firm*—McDermott Will & Emery LLP

(57) ABSTRACT

The present invention is directed to the topical application of the malonamide ACAT inhibitors described by Formula I. Other aspects of the invention are directed to topical formulations of these diamides, their use to treat sebaceous gland disorders and their use to alleviate oily skin.

3 Claims, No Drawings

METHOD FOR DECREASING SEBUM PRODUCTION

CROSS REFERENCE TO RELATED APPLICATION

This application claims the benefit of U.S. Provisional Application 60/509,984 filed Oct. 9, 2003.

FIELD OF THE INVENTION

The present invention is directed to the topical application of a class of diamide ACAT inhibitors. Other aspects of the invention are directed to topical formulations of these diamides, their use to treat sebaceous gland disorders and their use to alleviate oily skin.

BACKGROUND OF THE INVENTION

Human skin is composed of three primary layers, the stratum corneum, the epidermis, and the dermis. The outer layer is the stratum corneum. Its primary function is to serve as a barrier to the external environment. Lipids are secreted to the surface of the stratum corneum. These lipids decrease the stratum corneum's water permeability. Sebum typically constitutes 95% of these lipids. Abramovits et al, Dermatologic Clinics, Vol 18, Number 4, October 2000.

Sebum is produced in the sebaceous glands. These glands are present over most of the surface of the body. The highest concentration of these glands occurs on the scalp, the forehead and the face. Despite the important physiological role that sebum plays, many individuals experience excess sebum production, especially in the facial area. Excess sebum is associated with an increased incidence of acne. Even in individuals without acne, sebum can make the skin look greasy, decreasing its attractiveness. Abramovits et al, supra.

Current treatments for excess sebum are less than optimal. Accutane (isotretinoin) reduces sebum secretion by up to 90%. However, isotretinoin is associated with a number of serious side effects. It causes serious birth defects and is contraindicated in women of childbearing age. Thus, isotretinoin is only utilized for severe acne. It is inappropriate to use this drug merely as a cosmetic aid.

Acyl CoA cholesterol acyl transferase (ACAT) inhibitors were initially evaluated to treat elevated cholesterol. U.S. Pat. No. 6,133,326 discloses that ACAT inhibitors also reduce the secretion of sebum. While the '326 patent is a valuable contribution to the art, such treatments are not commercially available at the present time. Currently, the most practical means of alleviating excess sebum is frequent washings. Thus, a need exists in the art for new treatments that will reduce the secretion of sebum by the sebaceous glands.

SUMMARY OF THE INVENTION

A new method for decreasing the secretion of sebum, by the sebaceous glands, has been discovered. A class of ACAT inhibitors that exhibit superior activity in the inhibition of sebum secretion has been discovered. These ACAT inhibitors may be represented by Formula I:

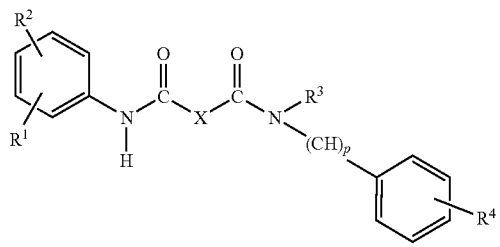

Formula I in which $R^1$ and $R^2$ are each independently represented by hydrogen, $C_{1-6}$ alkyl, $C_{1-6}$ alkoxy, halogen, hydroxy, trifluoromethyl, trifluoromethoxy, cyano, $NR^5R^6$, or $SR^7$; X is represented by —$CR^8R^9$—$(CH_2)_n$-; $R^3$ is represented by hydrogen, $C_{1-6}$ alkyl, —$(CH_2)_q$-Ph, or —$(CH_2)_q$-M; p is represented by an integer from 1 to 4; $R^4$ is represented by a substituent selected from the group consisting of hydrogen, $C_{1-6}$ alkyl, $C_{1-6}$ alkoxy, halogen, hydroxy, trifluoromethyl, trifluoromethoxy, cyano, $NR^5R^6$, and $SR^7$; $R^5$, $R^6$, $R^7$, $R^8$, and $R^9$ are each independently represented by hydrogen or $C_{1-6}$ alkyl; Ph is represented by a phenyl ring which may be optionally substituted; M is represented by a 5- or 6-membered heteroaryl ring, containing 1 hetero-atom selected from the group N, S, or O; n and q are each independently represented by an integer from 0-4; a pharmaceutically acceptable salt thereof, or a prodrug thereof.

The compounds of Formula I may be administered to a patient to decrease the amount of sebum secreted by their sebaceous glands. Typically, the compounds will be administered topically to the areas exhibiting excess sebum production. Decreasing sebum secretion will alleviate a number of dermatological disorders and cosmetic complaints. These conditions include oily skin, oily hair, shiny skin, acne, and seborrheic dermatits.

The invention is also directed to pharmaceutical compositions containing at least one of the compounds of Formula I in admixture with a carrier suitable for topical administration. In a further embodiment, the invention is directed to an article of manufacture containing a compound of Formula I, packaged for retail distribution, in association with instructions advising the consumer on how to use the compound to alleviate a condition associated with excess sebum production. An additional embodiment is directed to the use of a compound of Formula I as a diagnostic agent to detect inappropriate sebum production. Other aspects of the invention are directed to the use of a compound of Formula I in the manufacture of a medicament for seborrhea.

DETAILED DESCRIPTION OF THE INVENTION

The headings within this document are only being utilized expedite its review by the reader. They should not be construed as limiting the invention or claims in any manner.

A) Definitions and Exemplification

As used throughout this application, including the claims, the following terms have the meanings defined below, unless specifically indicated otherwise. The plural and singular should be treated as interchangeable, other than the indication of number:

a. "$C_1$-$C_6$ alkyl" refers to a branched or straight chained alkyl group containing from 1 to 6 carbon atoms, such as methyl, ethyl, n-propyl, isopropyl, n-butyl, isobutyl, n-pentyl, isopentyl, n-hexyl, 1,1-dimethylbutyl, 2,3-dimethylbutyl, etc.

b. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, n-pentoxy, n-hexyloxy, etc.

c. "halogen" refers to a chlorine, fluorine or bromine atom.

d. "optionally substituted phenyl" refers to a phenyl (—$C_6H_5$) which may be substituted with up to 3 substituents, each substituent is independently selected from the group consisting of $C_{1-6}$ alkyl, $C_{1-6}$ alkoxy, halogen, hydroxy, trifluoromethyl, trifluoromethoxy, cyano, $NR^5R^6$, or $SR^7$. These substituents may be the same or different and may be located at any of the ortho, meta, or para positions.

e. "heteroaryl" refers to aromatic ring having a single heteroatom selected from oxygen, nitrogen and sulfur. More specifically, it refers to a 5-, or 6-, membered ring containing 1 nitrogen atom, 1 oxygen atom, or 1 sulfur atom. The 5-membered ring has 2 double bonds and the 6-membered ring has 3 double bonds. Examples of such heteroaryl ring systems include, but is not limited to pyrrolyl, furanyl, thiophenyl, and pyridinyl.

f. "pharmaceutically acceptable salts" is intended to refer to either pharmaceutically acceptable acid addition salts" or "pharmaceutically acceptable basic addition salts" depending upon actual structure of the compound.

g. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

h. "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

i. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

j. "compound of Formula I", "compounds of the invention" and "compounds" are used interchangeably throughout the application and should be treated as synonoms.

k. "patient" refers to warm blooded animals such as, for example, guinea pigs, mice, rats, gerbils, cats, rabbits, dogs, monkeys, chimpanzees, and humans.

l. "treat" refers to the ability of the compounds to either relieve, alleviate, or slow the progression of the patient's disease (or condition) or any tissue damage associated with the disease.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Any reference in this application to a compound of Formula I, is intended to cover the compounds individually, as mixtures, as salts, as solvates or any combination thereof.

All of the compounds of Formula I have at least two phenyl rings, as depicted immediately below:

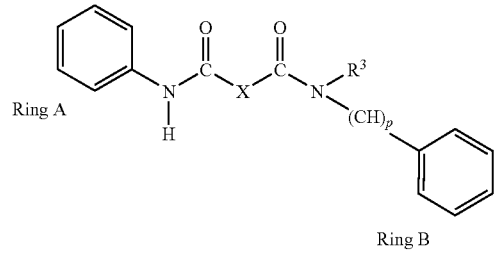

Ring A may be unsubstituted, or it may be substituted with one or two substituents as defined by $R^1$ and $R^2$. $R^1$ and $R^2$ may be represented by identical substituents, or different substituents. In one embodiment, $R^1$ and $R^2$ are each represented by isopropyl moieties and are both located at the ortho positions of the phenyl ring.

Ring B may also be optionally substituted, as listed for $R^4$. $R^4$ may represent up to 3 substituents, other than hydrogen, as described above. These substituents may be located at any of the ortho, meta, or para positions.

$R^3$ may also be represented may a phenyl ring or a phenylalkylene moiety. Any such phenyl ring may also be substituted with up to 3 substituents, as described above. They may be located at any of the ortho, meta, or para positions.

$R^3$ may also be represented by a heteroaryl ring or by a heteroarylalkylene moiety. The heteroaryl ring may be attached to the indicated nitrogen atom by any carbon atom of the heteroaryl ring. Likewise, if q is 1, 2, 3, or 4, then the heteroaryl ring may be bonded to the alkylene moiety via any of its carbon atoms.

In a further embodiment of the invention, Formula IA exemplifies a subgenus of Formula I, particularly useful for topical application.

FORMULA IA

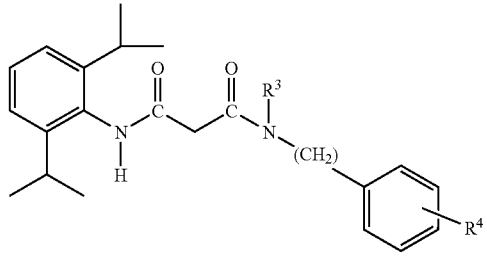

In Formula IA, $R^1$ and $R^2$ are each isopropyl (ortho), p is 1 and X is methylene, as exemplified above; $R^3$ is represented by $C_{1-6}$ alkyl or heteroaryl, (more typically isopropyl, or pyridyl) and $R^4$ is as defined in Formula I.

More specific examples of compounds of Formula Ia include:
a) N-benzyl-N'-(2,6-diisopropyl-phenyl)-N-isopropyl-malonamide;
b) N'-[2,6-bis(1-methylethyl)phenyl]-N-(1-methylethyl)-N-[[4-(methylthio)phenyl]methyl]-propanediamide and;
c) N-[2,6-bis(1-methylethyl)phenyl]-]β-[[(4-methoxyphenyl)methyl](2-pyridinyl)amino]-]β-oxo-propanamide.

B) Synthesis

The compounds of Formula I have previously been described in the literature. The reader's attention is directed to European Patent Application Number 0 433 662, which is hereby incorporated by reference. The '662 application discloses that the compounds of Formula I have acyl-coenzyme A cholesterol acyltransferase (ACAT) inhibitory activity. The '662 application discloses that these compounds can be used to lower elevated cholesterol levels and to treat atherosclerosis. The '662 application does not disclose using these compounds to decrease sebum secretion.

The '662 application discloses how to prepare the compounds of Formula I. The reader's attention is directed to pages 7-20 where methods for synthesizing these compounds are described. Methods for preparing pharmaceutically acceptable salts of these compounds are described on page 6 of the specification.

C) Medical and Cosmetic Uses

Inhibition of acyl-CoA cholesterol acyl transferase (ACAT) blocks the esterification of free cholesterol-to-cholesterol esters. Cholesterol esters are the primary transportation and storage form of cholesterol in animals. In the intestines, ACAT inhibitors have been shown to inhibit the absorption of cholesterol from the gut. In the liver, inhibition of ACAT has been shown to decrease the formation and secretion of cholesterol-containing lipoproteins by decreasing the cholesterol ester mass of the lipoprotein core. For these reasons, ACAT inhibitors have previously been evaluated as a means to lower serum cholesterol levels.

Dermal sebaceous glands are holocrine glands that secrete a mixture of lipids known as sebum. Sebum is composed of triglycerides, wax, sterol esters and squalene. There is considerable variation in the composition of human sebum based on individual variables such as age, sex, diet, and disease. Sebum is produced in the acinar cells of sebaceous glands, accumulates as those cells age and migrates towards the center of the gland. At maturation, the acinar cells lyse and release sebum into the lumenal duct, from which the sebum is secreted.

Formation of sebum is regulated by a variety of hormones that act primarily to regulate the rate of lipid metabolism. Waxes and sterols are converted, within acinar cells, to a stable ester form for storage via the activity of a variety of acyl and fatty acid transferases. These esters are then stored in lipid droplets within the acinar cells prior to release.

The compounds of formula I block the conversion of free cholesterol-to-cholesterol ester, leading to increased levels of free cholesterol within the acinar cells. While the cellular mechanism is not fully understood at the present time, the acinar cells produce less sebum when contacted with an ACAT inhibitor.

Thus, the compounds of formula I inhibit the secretion of sebum and thus reduce the amount of sebum on the surface of the skin. The compounds can be used to treat a variety of dermal diseases such as acne or seborrheic dermatitis.

In addition to treating diseases associated with excess sebum production, the compounds can also be used to achieve a cosmetic effect. Some consumers believe that they are afflicted with overactive sebaceous glands. They feel that their skin is oily and thus unattractive. These individuals can utilize the compounds of Formula I to decrease the amount of sebum on their skin. Decreasing the secretion of sebum will alleviate oily skin in individuals afflicted with such conditions.

In order to exhibit the biological effects described above, the compounds need to be administered in a quantity sufficient to inhibit production and/or secretion of sebum by the sebaceous glands and acinar cells. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally), rectally, or topically.

In a typical embodiment, the compounds are administered topically. Topical administration is especially appropriate for acne and for cosmetic indications. The compound will be applied to those areas of the skin afflicted with excess sebum production. The dose will vary, but as a general guideline, the compound will be present in a dermatologically acceptable carrier in an amount of from 0.01 to 10 w/w % and the dermatological preparation will be applied to the affected area from 1 to 4 times daily. "Dermatologically acceptable" refers to a carrier which may be applied to the skin, hair or scalp, and which will allow the drug to diffuse to the site of action. (i.e. the sebaceous glands and/or the acinar cells).

D) Co-Administration

In a further embodiment of the invention, the compounds of Formula I can be co-administered with other compounds to further enhance their activity, or to minimize potential side effects. For example, antibiotics, such as tetracycline and clindamycin, have been used to alleviate acne. The antibiotic eradicates the microorganism, Propionbacterium acnes, leading to a reduction in the patient's acne. The compounds of Formula I can be co-administered with any antibiotic suitable for the treatment of acne.

Retinoids, such as isotretinoin, have been shown to decrease sebum production and are used to treat acne. These retinoids can be co-administered with a compound of Formula I in order to decrease sebum production and/or to treat acne.

Estrogen and progesterone have each been shown to decrease sebum production. These compounds, or any synthetic agonist of the estrogen or progesterone receptor, may be co-administered with a compound of formula I in order to decrease sebum production.

Anti-androgens have been shown to decrease sebum secretion. Anti-androgens can work by a number of different mechanisms. For example, some compounds block the conversion of testosterone to 5-α-dihydrotestosterone, which is responsible for the biological effect in many tissues. 5-Alpha-reductase inhibitors, such as finasteride, have been shown to decrease sebum production. Finasteride is commercially available from Merck under the trade name Propecia®. Examples of other 5-α-reductase inhibitors include dutasteride (Glaxo Smithkline). Other anti-androgens are antagonists of the androgen receptor. For example, androgen antagonists, such as flutamide, have been reported to decrease sebum production. Such compounds can be co-administered with the compounds of Formula I to decrease sebum production.

As used in this application, co-administered refers to administering a compound of Formula I with a second medicinal, typically having a differing mechanism of action, using a dosing regimen that promotes the desired result. This can refer to simultaneous dosing, dosing at different times during a single day, or even dosing on different days. The compounds can be administered separately or can be combined into a single formulation. Techniques for preparing such formulations are described below.

E. Cosmetic and Pharmaceutical Formulations

If desired, the compounds can be administered directly without any carrier. However, to ease administration, they will typically be formulated into pharmaceutical carriers For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

Typically however, the compounds will be incorporated into formulations suitable for topical administration. Any of the topical formulations known in the art may be used. Examples of such topical formulations include lotions, sprays, creams, ointments, salves, gels, etc. Actual methods for preparing topical formulations are known or apparent to those skilled in the art, and are described in detail in Remington's Pharmaceutical Sciences, 1990 (supra); and Pharmaceutical Dosage Forms and Drug Delivery Systems, 6th ed., Williams & Wilkins (1995).

In a further embodiment, the formulations described above may be packaged for retail distribution (i.e., a kit or article of manufacture). The package will contain instructions advising the patient how to use the product to alleviate conditions such as acne, oily skin, etc. Such instructions may be printed on the box, may be a separate leaflet or printed on the side of the container holding the formulation, etc.

The compounds of Formula I may also be admixed with any inert carrier and utilized in laboratory assays in order to determine the concentration of the compounds within the serum, urine, etc., of the patient as is known in the art. The compounds may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data are being presented in order to further illustrate the invention. This disclosure should not be construed as limiting the invention in any manner.

EXAMPLE I

Luderschmidt et al describes an animal model for testing whether compounds are capable of modulating sebum secretion. Arch. Derm. Res. 258, 185-191 (1977). This model uses Syrian hamsters, whose ears contain sebaceous glands. Compounds can be administered to these animals to determine if a test agent is capable of modulating sebum production A series of compounds known to inhibit ACAT were screened using methods analogous to those of Luderschmidt et al. Table IA shows the results obtained with selected diamides encompassed by Formula I above. Table IB shows the results obtained with a series of diamides not encompassed by Formula I. Formula IC shows the results obtained with other potent ACAT inhibitors that are not diamidess.

Tables IA-IC also reports the affinity of the compound for rat ACAT, measured as an $IC_{50}$. These values were determined by measuring the ACAT-mediated transfer of tritiated oleic acid from acyl-CoA to cholesterol to give labeled cholesteryl oleate. The source of ACAT activity was homogenates of rat intestinal tissue. Predetermined concentrations of: 1) intestinal homogenate containing endogenous cholesterol, 2) test compound, and 3) $[1\text{-}^{14}C]$ oleolyl-CoA were contacted for a predetermined time. The reaction was quenched and the results were determined by thin layer chromatography. Analogous assays using rabbit intestine were described by Roth et al in J. Med Chem. 35:1609-1617(1992).

Testing for sebum inhibition was carried out in the following manner. Male Syrian hamsters aged 9 to 10 weeks were introduced into the laboratory environment and acclimated for 2 weeks prior to use in the study. Each group consisted of 5 animals and were run in parallel with vehicle and positive controls. Prior to administration, 10 mg of each compound was dissolved in 1 mL of Universal solvent (ethanol/propylene glycol (70/30% v/v) to achieve a final concentration of 1 w/v %.

Animals were dosed topically twice daily, five days a week, for 4 weeks. Each dose consisted of 25 micro liters of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8 mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at $-80°$ C. under nitrogen until HPLC analysis. In addition to ear samples, an aliquot of each drug and vehicle (at least 250 ul) was also stored at $-80°$ C. for inclusion in the HPLC analysis.

HPLC analysis was carried out on an extract of the tissue sample. Tissue samples were contacted with 3 ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at 37° C., under nitrogen, for approximately 1 hour, and then lyophilized for approximately 48 hours. The samples were then removed from the lyophilizer and each vial was reconstituted with 600 μl of solvent A (trimethylpentane/tetrahydrofuran (99:1). The samples were then recapped and vortexed for 5 minutes.

200 μl of each sample was then transferred to a pre-labeled 200 μl HPLC vial with 200 μL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at 30° C. by the Agilent column heater unit. The HPLC autosampler was programmed to maintain the sample temperature at 20° C. throughout the run.

10 uL of each sample was injected in triplicate into the column. Two solvents were used for the solvent gradient. Solvent A was an admixture of trimethylpentane and tetrahydrofuran (99:1). Solvent B was ethylacetate. The gradient utilized is described in the table below:

| Time (min) | Solv A (%) | Solv B (%) | Flow (mL/min) |
|---|---|---|---|
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at 45° C. with a gain of 5, and $N_2$ pressure maintained at 3.1 bar. Analog signal obtained by the instrument was sent to the Agilent A/D interface module where it was converted to a digital output. The conversion was based on a 10000 mAU/volt set point and the data rate was set at 10 Hz (0.03 min). The resulting digital output was then feed into the Agilent ChemStation software for integration of the peak area.

The results of the HPLC analysis are reported below in Tables IA-C. The results are reported as the reduction in cholesterol ester (CE) and wax ester (WE) production, when compared to the vehicle control. A negative number indicates that the ACAT inhibitor actually increased production of sebum.

TABLE IA

Compounds of Invention

| Compound Number | Molecular Structure | ACAT Inhibition (IC 50) IAI (nM) | Change vs. relevant vehicle control % Reduction in CE | % Reduction in WE | Sum CE + WE |
|---|---|---|---|---|---|
| 1 | H₃C–CH₃ ... (structure) | 15 | 94% | 80% | 174% |

TABLE IA-continued

Compounds of Invention

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 1 * (tested multiple times) | [2,6-diisopropylphenyl-NH-C(O)-CH2-C(O)-N(isopropyl)(benzyl)] | 15 | 94% | 84% | 178% |
| 2 | [2,6-diisopropylphenyl-NH-C(O)-CH2-C(O)-N(isopropyl)(4-methylthiobenzyl)] | 26 | 65% | 31% | 96% |
| 3 | [2,6-diisopropylphenyl-NH-C(O)-CH2-C(O)-N(2-pyridyl)(4-methoxybenzyl)] | 31 | 51% | 33% | 84% |

TABLE IB

Comparative Examples-

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 4 | [2,6-diisopropylphenyl-NH-C(O)-CH2-C(O)-N(benzyl)(2-(dimethylamino)ethyl)] | 170 | −1% | −18% | −19% |

TABLE IB-continued

Comparative Examples-

| Compound Information | | ACAT Inhibition | Change vs. relevant vehicle control | | |
|---|---|---|---|---|---|
| Compound Number | Molecular Structure | (IC 50) IAI (nM) | % Reduction in CE | % Reduction in WE | Sum CE + WE |
| 5 | [structure: 2,6-diisopropylphenyl malonamide with N-(4-methoxybenzyl)-N-pyrimidin-2-yl] | 61 | 32% | −4% | 28% |
| 6 | [structure: 2,6-diisopropylphenyl malonamide with N-benzyl-N-(2-cyanoethyl)] | 72 | 23% | −1% | 22% |
| 7 | [structure: 2,6-diisopropylphenyl malonamide with N-phenyl-N-(ethoxycarbonylmethyl)] | 26 | −67% | −84% | −151% |
| 8 | [structure: 2,6-diisopropylphenyl malonamide with N-isopropyl-N-phenyl] | 14 | −27% | −70% | −97% |

TABLE IC

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 9 | [structure: 2,6-diisopropylphenyl amide of 3-oxo-5,5-diphenylpentanoic acid] | 44 | 7% | 2% | 9% |
| 10 | [structure: 2,6-diisopropylphenyl amide with tetrazole bearing long alkyl chain and phenyl] | 8 | −105% | −147% | −252% |
| 11 | [structure: long alkyl chain-tetrazole-CH(phenyl)-C(O)NH-2,4,6-trimethoxyphenyl] | 8.5 | −5% | −6% | −11% |
| 12 | [structure: 2,6-diisopropylphenyl amide with phosphinate bearing phenyl and undecyl chain] | 15 | 48% | 44% | 92% |
| 13 | [structure: 2,6-diisopropylphenyl urea with (4-phenyltetrahydropyran-4-yl)methyl group] | 42 | −7% | −7% | −14% |

TABLE IC-continued

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 14 | 2,6-diisopropylphenyl-NH-C(O)-CH₂-C(O)-(CH₂)₁₁-CH₃ | 6 | −8% | −15% | −23% |
| 15 | 2,6-diisopropylphenyl-NH-C(O)-[tetrahydropyran-2-one-3-yl with 6-heptyl substituent] | 3.4 | 24% | 14% | 38% |
| 16 | 2,6-diisopropylphenyl-NH-C(O)-NH-CH₂-[1-(4-hydroxymethylphenyl)cyclopentyl] | 26 | −1% | 0% | −1% |
| 17 | 2,6-diisopropylphenyl-NH-C(O)-NH-CH₂-[1-(pyridin-2-yl)cyclopentyl] | 16 | −56% | −64% | −120% |
| 18 | 1,3,5-trimethylpyrazol-4-yl-NH-C(O)-CH₂-[tetrazol-5-yl]-N-(CH₂)₁₁-CH₃ | 17 | −23% | −49% | −72% |
| 19 | 2,6-diisopropylphenyl-NH-C(O)-NH-CH₂-[tetrazol-5-yl]-N-(CH₂)₁₁-CH₃ | 12 | −6% | 1% | −5% |

TABLE IC-continued

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 20 | [structure: 2,6-diisopropylphenyl urea linked to CH2-cyclobutyl-furan] | 32 | 4% | −1% | 3% |
| 21 | [structure: 2,6-diisopropylphenyl urea linked to chiral CH2-CH(Ph)-NH-CH2-(2-methoxyphenyl)] Chiral | 45 | 4% | 3% | 7% |
| 22 | [structure: 2,4-difluorophenyl urea with N-octyl and N-(CH2)5-S-(4,5-diphenylimidazol-2-yl)] | 22 | 20% | 4% | 24% |
| 23 | [structure: 2,6-diisopropylphenyl urea linked to CH2-cyclopentyl-(3-phenyl)-CH2-N(CH2CH2OH)2] | 47 | 4% | −84% | −80% |
| 24 | [structure: 2,6-diisopropylphenyl urea linked to CH2-cyclopentyl-(3-phenyl)-CH2-morpholine] | 11 | 20% | 1% | 21% |

TABLE IC-continued

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 25 | (structure) | 17 | 10% | −3% | 7% |
| 26 | (structure) | 32 | 28% | 9% | 37% |
| 27 | (structure) | 35 | −17% | −23% | −40% |
| 28 | (structure) | 18 | 0% | −8% | −8% |
| 29 | (structure) | 48 | 19% | 11% | 30% |

TABLE IC-continued

| Compound Information | | ACAT Inhibition (IC 50) IAI (nM) | Change vs. relevant vehicle control | | |
|---|---|---|---|---|---|
| Compound Number | Molecular Structure | | % Reduction in CE | % Reduction in WE | Sum CE + WE |
| 30 | [structure: 2,6-diisopropylphenyl urea linked to methoxy-tetrahydronaphthalene] | 17 | −10% | −34% | −44% |
| 31 | [structure: 2,6-diisopropylphenyl urea linked to tryptamine] | 43 | 9% | 9% | 18% |

Tables IA, IB and IC summarize the results obtained in the experiments described above. Table IA shows the results obtained with compounds encompassed by Formula I (i.e. the invention). Tables IB and IC are included for comparative purposes and include compounds not described by Formula I. Table IB shows diamides structurally related to those of Formula I. Table IC shows the results obtained with known ACAT inhibitors, not structurally related to the diamides, but having an $IC_{50}$ of 50 nm, or less, when measured in the ACAT assay described supra.

To expedite this comparison a common format was used in the three tables. Each compound was assigned an arbitrary compound number, which is shown in the far left column (i.e. column #1). The second column shows the structure of the compound tested and the third column shows its potency as an ACAT inhibitor in the assay supra.

Columns 4 through 6 shows the results the compounds had on the secretion of sebum. The results are expressed as the difference from the control. A positive number reflects a decrease in the production of the sebum component being measured, i.e. cholesterol ester(CE) or wax ester(WE). A negative number indicates that the compound increased the production of CE or WE.

Column 4 shows the compounds ability to reduce the amount of cholesterol ester in the sebum sample. Inhibition of cholesterol ester is important because ACAT is responsible for the conversion of cholesterol to cholesterol ester. These results reflect the compounds ability, or lack thereof, to modulate ACAT in the target tissue (hamster sebaceous glands).

Column 5 shows the effect the compound had on the generation of wax ester. Wax esters are specific markers of the sebaceous glands and are not appreciably detected in any other layer of the skin. Reduction of wax ester reflects a decrease in sebum secretion. Columns 6 is a summation of the results expressed in columns 4 and 5 (and is included to further elucidate relative differences in activity).

As shown in Table IA, the diamides of Formula I significantly decreased the secretion of cholesterol ester, indicating that ACAT was being inhibited in the target tissue. Wax ester was also decreased indicating that total sebum secretion was diminished when compared to the control. For example compound #1 decreased CE by 95% and WE by 80%. Compounds 2 and 3 produced comparable results.

A comparison with Table IB shows significant differences. Despite the structural similarity, these diamides had significantly less impact on CE and WE secretion.

A comparison with the compounds of Table IC is also illustrative. These compounds are all potent ACAT inhibitors. All had $IC_{50}$'s of 50 nm, or less. Despite this potency, as a group, they had significantly less effect on sebum secretion than the compound of Formula I. Such results were unexpected.

What is claimed is:

1. A method for decreasing sebum secretion comprising the topical administration of an effective amount of N-benzyl-N'-(2,6-diisopropyl-phenyl)-N-isopropyl-malonamide, or a pharmaceutically acceptable salt thereof, to a patient in need thereof.

2. A method for alleviating oily skin comprising the topical administration of an effective amount of N-benzyl-N'-(2,6-diisopropyl-phenyl)-N-isopropyl-malonamide, or a pharmaceutically acceptable salt thereof, to a patient in need thereof.

3. A method for treating acne comprising the topical administration of an effective amount of N-benzyl-N'-(2,6-diisopropyl-phenyl)-N-isopropyl-malonamide, or a pharmaceutically acceptable salt thereof, to a patient in need thereof.

* * * * *

UNITED STATES PATENT AND TRADEMARK OFFICE
CERTIFICATE OF CORRECTION

PATENT NO. : 7,615,230 B2 Page 1 of 1
APPLICATION NO. : 10/958306
DATED : November 10, 2009
INVENTOR(S) : Kostlan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1366 days.

Signed and Sealed this

Nineteenth Day of October, 2010

David J. Kappos
*Director of the United States Patent and Trademark Office*